United States Patent [19]

Pham et al.

[11] Patent Number: 5,663,474
[45] Date of Patent: Sep. 2, 1997

[54] ALKYLATION PROCESS USING HYDROGEN FLUORIDE-CONTAINING ALKYLATION CATALYSTS

[75] Inventors: Hang Thanh Pham, Amherst, N.Y.; Robert Pratt, Randolph, N.J.; Charles Lewis Redmon, Orchard Park, N.Y.; John James Thompson, Kenmore, N.Y.; Michael Van Der Puy, Amherst, N.Y.; Rajiv Ratna Singh, Getzville, N.J.; William James Hague, Montville, N.J.; Harold John Kieta, Buffalo, N.Y.; Matthew Hermes Luly, Lancaster, N.Y.; Jeffrey Warren McKown, East Aurora, N.Y.

[73] Assignee: AlliedSignal Inc., Morris County, N.J.

[21] Appl. No.: 612,041

[22] Filed: Mar. 7, 1996

[51] Int. Cl.⁶ .................. C07C 2/58; C07C 2/64
[52] U.S. Cl. ............. 585/721; 585/446; 585/462; 585/464; 585/458; 585/709; 585/723; 585/724; 585/725; 585/730; 585/731
[58] Field of Search .................. 585/709, 721, 585/723, 724, 725, 730, 731, 446, 462, 464, 458

[56] References Cited

U.S. PATENT DOCUMENTS

| | | | |
|---|---|---|---|
| 1,470,772 | 10/1923 | Simon et al. | |
| 2,430,181 | 11/1947 | Linn | 585/724 |
| 2,903,345 | 9/1959 | Hedley et al. | 41/42 |
| 3,591,432 | 7/1971 | Vazirani | 156/3 |
| 3,635,836 | 1/1972 | Mullen | 252/316 |
| 4,210,460 | 7/1980 | Seidenberger | 134/7 |
| 4,297,257 | 10/1981 | Elias et al. | 160/29.6 H |
| 4,373,050 | 2/1983 | Steinbrecher et al. | 524/405 |
| 4,383,868 | 5/1983 | Braley | 134/7 |
| 5,073,363 | 12/1991 | Pellico | 424/49 |
| 5,073,674 | 12/1991 | Olah | 585/725 |
| 5,277,881 | 1/1994 | Patridge, Jr. et al. | 422/241 |

FOREIGN PATENT DOCUMENTS

| | | |
|---|---|---|
| 638531A1 | 2/1995 | European Pat. Off. |
| 271324 | 8/1989 | Germany |
| 1572032 | 7/1980 | United Kingdom |

OTHER PUBLICATIONS

G. G. Hawley. *The Condensed Chemical Dictionary*. Tenth Edition. Van Nostrand Reinhold Company (1981) New York. pp. 20, 559.

Gordon K. Braley, "Several Remedies for the Treatment of Spillages of Liquid Hazardous Chemicals", Proceedings of the 1980 National Conf. on Control of Hazardous Material Spills (May 13–15, 1980 Louisville, Kentucky), pp. 103–108.

Jache, Albert W. and Cady, George H. "Solubility of Fluorides of Metals in Liquid Hydrogen Fluoride" *J. Phys. Chem.* 56 (1952) 1106.

Chem. Abst. 120:57882q "Manufacture of Gaseous Hydrogen Fluoride" SU 1,566,651 (Dec. 7, 1992).

*Primary Examiner*—Glenn A. Caldarola
*Assistant Examiner*—Thuan D. Dang
*Attorney, Agent, or Firm*—Lois A. Gianneschi

[57] ABSTRACT

This invention relates to catalysts for alkylation reactions and their preparation. More particularly, the invention relates to an alkylation process using a hydrogen fluoride-containing alkylation catalyst, which catalyst may be safely and easily handled, transported, and stored.

21 Claims, No Drawings

ALKYLATION PROCESS USING HYDROGEN FLUORIDE-CONTAINING ALKYLATION CATALYSTS

FIELD OF THE INVENTION

This invention relates to catalysts for alkylation reactions and their preparation. More particularly, the invention relates to an alkylation process using a hydrogen fluoride-containing alkylation catalyst, which catalyst may be safely and easily handled, transported, and stored.

BACKGROUND OF THE INVENTION

Alkylation reactions are acid catalyzed reactions in which an alkyl group is incorporated into an organic molecule. The alkylated organic molecules, or alkylates, resulting from the reaction may be used as octane number enhancing components for gasoline or in detergent formulations.

A widely used catalyst in alkylation reactions is hydrogen fluoride. Hydrogen fluoride is advantageous in that its chemical stability makes it suitable for use over a wide range of conditions. However, hydrogen fluoride is disadvantageous in that it is a volatile substance. U.S. Pat. No. 5,073,674 discloses a method for decreasing hydrogen fluoride volatility by using complexes of ammonia or amine polyhydrogen fluoride. This method is undesirable due to the toxicity of the complexes. Thus, a need exists for a hydrogen fluoride alkylation catalyst that overcomes the disadvantages of both pure hydrogen fluoride and the prior art complexes.

DESCRIPTION OF THE INVENTION AND PREFERRED EMBODIMENTS

This invention provides an alkylation process that uses hydrogen fluoride-containing alkylation catalysts, in both solid and liquid forms. The catalysts of the invention are less hazardous than pure hydrogen fluoride and can be safely and easily stored, handled and transported. In addition, methods for preparation of the hydrogen fluoride-containing alkylation catalysts are provided.

The alkylation process of the invention comprises: (A) contacting a hydrogen fluoride-containing alkylation catalyst, comprising an effective amount of a carrier and a catalytic amount of hydrogen fluoride, with a feedstock under conditions suitable to form a reaction mixture comprising a hydrocarbon phase and a catalyst phase; (B) separating the reaction mixture into its hydrocarbon and catalyst phases; and (C) processing the hydrocarbon phase to recover the alkylate. By hydrogen fluoride-containing alkylation catalyst is meant an alkylation catalyst comprising hydrogen fluoride and a carrier.

A carrier, as that term is used for purposes of this invention, is a material that is not itself a reactant in the alkylation reaction and that does not form a complex with hydrogen fluoride. Further, when combined with hydrogen fluoride, the carrier serves to lower the vapor pressure of the hydrogen fluoride below that of pure hydrogen fluoride without altering the hydrogen fluoride's chemical properties. Suitable carriers for use in this invention include acid salts and polymers.

The acid salts useful as carriers are salts of acids which have a pKa value of about 7 or less, preferably about 4 or less, more preferably about 0 or less, and are soluble in hydrogen fluoride. Exemplary acids include, without limitation, carboxylic acids such as formic, propionic, and trifluoroacetic acids, sulfonic acids such as methanesulfonic and trifluoromethanesulfonic acids, and inorganic acids such as phosphoric, nitric, and sulfuric acids. Preferably, strong acids such as trifluoroacetic, sulfuric or sulfonic are used. The acid salt counterion may be any counterion that forms a salt with the acid selected which salt is soluble in hydrogen fluoride. By soluble in hydrogen fluoride is meant that the acid salt dissolves, or forms a homogeneous solution, in about ten times its weight or less of hydrogen fluoride. The counterion may be ammonium, alkyl ammonium such as tetramethyl- or tetraethylammonium, or an alkali metal (Group IA) cation. Illustrative salts include, without limitation, ammonium sulfate, potassium formate, sodium propionate, ammonium trifluoroacetate, and ammonium methanesulfonate. Preferably, ammonium sulfate, ammonium methanesulfonate, or ammonium trifluoroacetate is used.

Alternatively, the carrier may be a polymer. By the term polymer is meant homopolymers, copolymers, and mixtures thereof. Generally, the polymers used in the invention have molecular weights of from about 5,000 to 10,000,000. Preferably, polymers with molecular weights of from about 5,000 to about 1,000,000 are used.

The polymers useful in the hydrogen fluoride-containing alkylation catalysts of the invention are water-soluble polymers. By "water-soluble polymer" is meant any high molecular weight compound that swells, to about twice its dry volume, or dissolves with the addition of water at room temperature. Preferably, the polymers used in the catalysts are polymers that swell to about twice their dry volume on the addition of water.

Water-soluble polymer is meant to include semi-synthetic water-soluble polymers, synthetic water-soluble polymers, and mixtures thereof. Semi-synthetic water-soluble polymers are natural water-soluble polymer derivatives. Synthetic water-soluble polymers are not natural water-soluble polymer derivatives and are formed only through chemical reactions.

Exemplary semi-synthetic water-soluble polymers include, without limitation, cellulose ethers, modified starches, starch derivatives, natural gum derivatives, and mixtures thereof. Illustrative synthetic water-soluble polymers include, without limitation, polymers, related polymers, and polymer salts of acrylamide, acrylic acid, ethylene oxide, methacrylic acid, polyethyleneimine, polyvinyl alcohol, polyvinyl pyrrolidone, and mixtures thereof. By related polymer is meant that the polymer repeat unit, or a branch thereof, is extended by carbon atoms, preferably from one to four carbon atoms. For example, a related polymer of acrylic acid is one in which the vinyl group is extended by one carbon to form an allyl group.

Preferably, a synthetic water-soluble polymer is used. More preferably, polyacrylic acid or one of its salts is used. Most preferably, the water-soluble polymer is sodium polyacrylate.

To prepare the catalyst of the invention, an effective amount of carrier is mixed with a catalytic mount of hydrogen fluoride. Mixing may be performed in any suitable corrosion resistant vessel. If the carrier selected is an acid salt, the acid salt is mixed and dissolved in the hydrogen fluoride. If the carrier is a water soluble polymer, the water-soluble polymer is mixed with hydrogen fluoride to form an intimate mixture. The polymer may be in any form for mixing with hydrogen fluoride including, without limitation, granules, beads, pellets, fibers, or mats. Mixing may be accomplished by any means convenient, including without limitation stirring or dispersing the polymer into a pool of hydrogen fluoride or passing hydrogen fluoride gas over the polymer. Typically mixing is performed at temperatures from about 0 to about 100° C., preferably from about 10 to about 40° C. Pressure is not critical.

When the carrier is an acid salt, an effective amount of acid salt is an amount both capable of decreasing the volatility of the hydrogen fluoride to the desired level below that of pure hydrogen fluoride and which is dissolvable in the catalytic amount of hydrogen fluoride used. An effective amount of polymer is an amount capable of decreasing the volatility and increasing the surface tension of the catalytic amount of hydrogen fluoride used to the desired extent. The specific amount of acid salt or polymer used will depend on both the acid salt or polymer selected and the catalytic amount of hydrogen fluoride used.

A catalytic amount of hydrogen fluoride is an amount of hydrogen fluoride sufficient to maintain the desired level of catalytic activity in the specific alkylation reaction in which it is used. If the carrier is an acid salt, the minimum amount of hydrogen fluoride used is an amount effective both to dissolve the acid salt and to maintain the desired level of catalytic activity. For polymer carriers, the minimum amount of hydrogen fluoride is an amount effective to form an intimate mixture with the polymer and to maintain the desired catalytic activity.

Generally, regardless of the carrier selected, the amount of hydrogen fluoride used is from about 20 to about 99, preferably from about 30 to about 98, weight percent based on the total weight of the alkylation catalyst. For HF/polymer catalysts, more preferably from about 60 to about 99 weight percent and most preferably from about 70 to about 99 weight percent of hydrogen fluoride is used. For HF/acid salt catalysts, more preferably from about 50 to about 80 weight percent, most preferably from about 60 to about 75 weight percent, hydrogen fluoride is used. If a very small amount of hydrogen fluoride is used, the vapor pressure will be very low, but so too the catalytic activity. If a large amount of hydrogen fluoride is used, the vapor phase reduction will be less, but the catalytic activity high. One ordinarily skilled in the art will recognize that a balance preferably is achieved between using too little and too great an amount of hydrogen fluoride.

Without departing from the scope of the invention, it will be recognized that other components may be included in the catalysts of the invention. In general, any component that does not deleteriously effect the catalytic action or undesirably increase the volatility of the hydrogen fluoride may be used.

The hydrogen fluoride may be commercially available anhydrous hydrogen fluoride having a water content of 0.1% or less or aqueous hydrogen fluoride. Preferably, anhydrous hydrogen fluoride is used. The acid salt is preferably substantially anhydrous having a water content of less than about 1%. A number of substantially anhydrous acid salts are commercially available or such salts may be produced by using any of the well known drying techniques such as desiccant or vacuum drying.

If the desired acid salt is not readily available or is expensive, the acid salt may be prepared by mixing the acid with a bifluoride salt to form the acid salt. Alternatively, the acid salt may be formed in situ by mixing together the acid, bifluoride salt and hydrogen fluoride.

The catalysts may be in liquid, gel-like solid or, solid form. The hydrogen fluoride weight percentage over which the catalyst will be liquid depends upon the carrier used. Generally, for ammonium salts of acids having pKa's of about 3 or less, the hydrogen fluoride/acid salt alkylation catalyst may be liquid even with an acid salt content of from about 20 to about 30 weight percent. Within the range of from about 5 to about 30 weight percent hydrogen fluoride, the hydrogen fluoride polymer alkylation catalyst will be a solid or gel-like solid, while at higher hydrogen fluoride concentrations, the catalyst most likely will be a liquid.

The choice of solid, gel-like solid, or liquid catalyst will depend on a number of factors including the specific alkylation reaction used, the scale of the reaction, and the desired processing of the product mixture. The solid alkylation catalysts are advantageous in that they may be removed from an alkylated product by simple filtration or decantation. Alkylations using the solid catalysts also may be amenable to a flow system in which the liquid feed materials to be alkylated are allowed to flow down a column containing the catalyst.

The catalysts of the invention may be used in conjunction with a solid support that is inert to the reaction condition of the specific alkylation reaction chosen. Suitable inert supports include, without limitation, carbon, fluorine treated or coated resins, metal chalcites or halides inert to hydrogen fluoride or that can be converted to hydrogen fluoride-inert compounds, and acid-resistant molecular sieves. Alternatively, an inert support may be prepared by coating a non-inert support with any suitable inert material such as antimony trifluoride or aluminum trifluoride. The supported catalyst may be prepared by any method known in the art.

The alkylation catalysts of the invention may be used in any of the well known alkylation reactions, which reactions are conducted over a wide range of conditions. The alkylation catalyst may be used in both liquid and vapor phase alkylation reactions. Preferably, the catalyst is used in its liquid or solid form for liquid phase reactions and in its solid phase for vapor phase reactions. The alkylation reactions may be carried out in batch, intermittent, or continuous mode.

In the process to produce an alkylate, a feedstock is contacted with the alkylation catalyst in step (A). The feedstock, or feedstocks, used will depend on the desired alkylate. Suitable feedstock include, without limitation, paraffinic or isoparaffinic hydrocarbons, aromatic hydrocarbons, olefins and mixtures thereof.

Exemplary paraffinic or isoparaffinic hydrocarbons include, without limitation, methane, butane, isobutane, isopentane, and the like. Aromatic hydrocarbons include, without limitation, benzene, alkyl benzenes, alkylene benzenes, and the like. Olefins suitable for use include both olefinic hydrocarbons and olefin-acting agents including, without limitation, $C_3$ to $C_5$ alkyl halides, $C_3$ to $C_6$ monoolefins, and the like. In the case of paraffin-olefin alkylation, the molar ratio of paraffinic, isoparaffinic, or aromatic hydrocarbon to olefin used is from about 1:1 to about 1:200, preferably from about 1:3 to about 1:50, more preferably from about 1:5 to about 1:25. The feedstock may contain any cracking inhibitor or moderator known in the art.

In step (A), the feedstock and catalyst are contacted and thoroughly mixed in an alkylation reactor made of any suitable material such as TEFLON®-lined carbon steel under conditions suitable to form a reaction mixture having hydrocarbon and catalyst phases. The conditions, i.e., time, temperature, and pressure, are those suitable for producing the desired alkylate. The precise conditions will depend upon the phase of reaction, feedstock selected as well as the desired alkylate and are readily determinable by one ordinarily skilled in the art. In general, the contacting step may be carried out at a temperature from about −100° C. to about 150° C., preferably from about −30° C. to about 100° C., more preferably from about −10° C. to about 80° C. and at pressures from about 15 psia to about 315 psia. Contact, or residence times, will be from about 0.05 seconds to about several hours.

The reaction mixture formed in step (A) is separated into its hydrocarbon phase, containing the alkylate product, and catalyst phases in step (B). The separation may be accomplished by any convenient method known in the art such as distillation. The catalyst phase may be recycled back to contact step (A).

Following separation, the hydrocarbon phase may be processed in a step (C) to recover the alkylate product as well as any remaining catalyst and unreacted hydrocarbon or olefin. The catalyst and unreacted hydrocarbon or olefin may be recycled to step (A). Typically, the processing is accomplished by any of the well known fractionation methods.

The invention will be clarified further by a consideration of the following examples that are meant to be purely exemplary.

EXAMPLES

Example 1

10 g of sodium polyacrylate, m. wt. 1,000,000 was weighed in a TEFLON®-lined autoclave at room temperature and, after cooling of the autoclave with dry ice, 34.7 g HF were loaded into the autoclave to form a gel-like solid alkylating catalyst. The catalyst formed was 78 weight percent HF and 22 weight percent sodium polyacrylate. Subsequently the autoclave was warmed to room temperature and then 40.1 g of isobutane and 20.7 g of isobutylene were added to the autoclave and heated to, and held at, 85° C. for 1 hour during which the mixture was stirred. The reactor was then cooled and the organic liquid analyzed by gas chromatography and mass spectography. Analysis indicated $C_5$ to $C_{13}$ saturated hydrocarbons, including isooctane.

Example 2

The procedure of Example 1 was used except that the catalyst was 95 weight percent HF and 5 weight percent sodium polyacrylate. The resulting catalyst was liquid phase. 29.5 g Isobutane and 20 g isobutylene were added and reacted with the catalyst as in Example 1. Analysis of the organic liquid indicated $C_5$ to $C_{13}$ saturated hydrocarbons, including isooctane.

Example 3

36 g of HF and 4 g of polyacrylic acid copolymerized with 50 weight percent maleic acid, m. wt. 50,000 and available from Aldrich Chemicals were loaded into an autoclave and mixed to form a catalyst of 90 weight percent HF and 10 weight percent polymer. To the resulting liquid phase catalyst was added 40 g isobutane and 20 g isobutylene and the mixture heated to and held at 75° C. and stirred. The reactor was cooled and the liquid phase containing organics was analyzed by GC and MS and found to contain typical alkylation products, including isooctane.

Example 4

The procedure of Example 3 was used except that a catalyst that was 90 weight percent HF and 10 weight percent sodium polyacrylate copolymerized with methyl methacrylate, m. wt. 15,000 and available from Aldrich Chemicals was substituted for the catalyst of Example 3. GC and MS analysis of the liquid phase containing organics found it to contain typical alkylation products, including isooctane.

Example 5

The procedure of Example 3 was followed except that a 95 weight percent HF and 5 weight percent sodium polyacrylate, m. wt. 1,000,000, catalyst was used and 20.5 g of propylene was substituted for the isobutylene of Example 3. Analysis of the liquid phase containing organics by GC and MS found it to contain typical alkylation products, including isooctane.

Example 6

The procedure of Example 3 was used except that a catalyst of 95 weight percent HF and 5 weight percent sodium polyacrylate, m. wt. 1,000,000, was used and 20.2 g of amylene was substituted for the isobutylene of Example 3. Analysis the liquid phase containing organics by GC and MS found it to contain typical alkylation products, including isooctane.

Example 7

The procedure of Example 3 was used except that a catalyst that was 70 weight percent HF and 30 weight percent ammonium sulfate was used and 20 g of amylene were used for the isobutylene of Example 3. Analysis of the liquid phase containing organics by GC and MS found it to contain typical alkylation products, including isooctane.

Example 8

10 g sodium polyacrylate are weighed in a TEFLON®-lined autoclave at room temperature and, after cooling of the autoclave with dry ice, 30 g HF are loaded into the autoclave to form a solid alkylating catalyst. The catalyst is 75 weight percent HF and 25 weight percent sodium polyacrylate. Subsequently, the autoclave is warmed to room temperature and then a gaseous 2:1 mixture of isobutane and isobutylene is drawn through the solid catalyst in the autoclave. The effluent from the autoclave is condensed in a trap chilled with acetone and dry ice and the collected organic liquid is analyzed by GC and MS. Analysis indicates $C_5$ to $C_{13}$ saturated hydrocarbons are present, including isooctane.

Example 9

Sodium acrylate is polymerized in the presence of the following solid inert supports: carbon, aluminum trifluoride and calcium fluoride. This results in the solid water-soluble polymer grafted, or supported, on the inert supports. 50 g of each of these catalysts are weighed in TEFLON®-lined autoclaves at room temperature and, after cooling of the autoclaves with dry ice, 30 g HF is loaded into each of the autoclaves to form solid alkylating catalysts. Subsequently, the autoclaves are warmed to room temperature and then a gaseous 2:1 mixture of isobutane and isobutylene is drawn through the solid catalysts in the autoclaves. The effluent from the each of the autoclaves is condensed in a trap chilled with acetone and dry ice and the collected organic liquid is analyzed by GC and MS. Analysis demonstrates the presence of $C_5$ to $C_{13}$ saturated hydrocarbons, including isooctane.

Example 10

The procedure of Example 1 is used except that the catalyst is 95 weight percent HF and 5 weight percent acrylic acid copolymerized with 10% acrylamide, 200,000 m. wt. available from Aldrich Chemicals. The resulting catalyst is liquid phase. 29.5 g isobutane and 20 g isobutylene are added and reacted with the catalyst as in Example 1. Analysis of the organic liquid indicates $C_5$ to $C_{13}$ saturated hydrocarbons including isooctane.

Example 11

The procedure of Example 1 is used except that a catalyst that is 60 weight percent HF and 40 weight percent methacrylic acid, m. wt. 200,000 is used. 30 g Isobutane and 20 g isobutylene are added and reacted with the catalyst as in Example 1. Analysis of the organic liquid indicates $C_5$ to $C_{13}$ saturated hydrocarbons including isooctane.

Example 12

The procedure of Example 1 is used except that the catalyst used is 70 weight percent HF and 30 weight percent polyvinyl alcohol, m. wt. 5,000. 30 g Isobutane and 20 g isobutylene are added and reacted with the catalyst as in Example 1. Analysis of the organic liquid indicates $C_5$ to $C_{13}$ saturated hydrocarbons including isooctane.

Example 13

The procedure of Example 1 is used except that the catalyst used is 99 weight percent HF and 1 weight percent polyvinyl pyrrolidone, m. wt. 1,000,000. The resulting catalyst is liquid phase. 30 g Isobutane and 20 g isobutylene are added and reacted with the catalyst as in Example 1. Analysis of the organic liquid indicates $C_5$ to $C_{13}$ saturated hydrocarbons including isooctane.

Example 14

The procedure of Example 1 is used except that the catalyst is 95 weight percent HF and 5 weight percent sodium polyethylene oxide, M. wt 250,000 is used. The resulting catalyst is liquid phase. 29.5 g Isobutane and 20 g isobutylene is added and reacted with the catalyst as in Example 1. Analysis of the organic liquid indicates $C_5$ to $C_{13}$ saturated hydrocarbons including isooctane.

Example 15

The procedure of Example 3 is used except that a catalyst that is 80 weight percent HF and 20 weight percent sodium fluoride is used and 20 g amylene is used for the isobutylene. Analysis of the liquid phase containing organics finds it to contain organics including isooctane.

Example 16

The procedure of Example 3 is used except that the catalyst used is 20 weight percent HF and 80 weight percent sodium propionate. Analysis of the liquid phase containing organics by GC and MS shows it to contain typical alkylation products, including isooctane.

Example 17

The procedure of Example 3 is used except that the catalyst used is 40 weight percent HF and 60 weight percent ammonium trifluoroacetate. Analysis of the liquid phase containing organics by GC and MS shows it to contain typical alkylation products, including isooctane.

Example 18

The procedure of Example 3 is used except that the catalyst used is 60 weight percent HF and 40 weight percent ammonium methanesulfonate. Analysis of the liquid phase containing organics by GC and MS shows it to contain typical alkylation products, including isooctane.

What is claimed is:

1. An alkylation process comprising the steps of:
    (A) contacting a feedstock and a hydrogen fluoride-containing alkylation catalyst, the catalyst comprising an effective amount of a carrier selected from the group consisting of a polymer and an acid salt that is ammonium sulfate, ammonium methanesulfonate, or ammonium trifluoroacetate and a catalytic amount of hydrogen fluoride, under conditions suitable to form a reaction mixture comprising a hydrocarbon phase, the hydrocarbon phase comprising an alkylate product, and a catalyst phase;
    (B) separating the hydrocarbon phase and the catalyst phase; and
    (C) processing the hydrocarbon phase to recover the alkylate product.

2. The process of claim 1 wherein the catalytic amount of hydrogen fluoride is from about 20 to about 99 weight percent based on the total weight of the alkylation catalyst.

3. The process of claim 1 wherein the catalytic amount of hydrogen fluoride is from about 30 to about 98 weight percent based on the total weight of the alkylation catalyst.

4. The process of claim 1 wherein the polymer is a water-soluble polymer.

5. The process of claim 4 wherein the water soluble polymer is a synthetic water soluble polymer.

6. The process of claim 4 wherein the water-soluble polymer is present in an amount of from about 40 to about 1 weight percent and the hydrogen fluoride is present in an amount of from about 60 to about 99 weight percent.

7. The process of claim 4 wherein the water-soluble polymer is present in an amount of from about 30 to about 1 weight percent and the hydrogen fluoride is present in an amount of from about 70 to about 99 weight percent.

8. The process of claim 1 wherein the acid salt is ammonium sulfate.

9. The process of claim 1 wherein the acid salt is ammonium methanesulfonate.

10. The process of claim 8 or 9 wherein the acid salt is present in an amount of from about 50 to about 20 weight percent and the hydrogen fluoride is present in an amount of from about 50 to about 80 weight percent.

11. The process of claim 8 or 9 wherein the acid salt is present in an amount of from about 40 to about 25 weight percent and the hydrogen fluoride is present in an amount of from about 60 to about 75 weight percent.

12. The process of claim 1 wherein the feedstock comprises at least one hydrocarbon selected from the group consisting of paraffinic hydrocarbon, isoparaffinic hydrocarbon, aromatic hydrocarbons, and mixtures thereof and at least one selected from the group consisting of $C_3$ to $C_5$ alkyl halides and $C_3$ to $C_6$ mono-olefins and mixtures thereof.

13. An alkylation process comprising the steps of:
    (A) contacting a feedstock, comprising at least one hydrocarbon selected from the group consisting of paraffinic hydrocarbon, isoparaffinic hydrocarbon, aromatic hydrocarbon, and mixtures thereof and at least one selected from the group consisting of $C_3$ to $C_5$ alkyl halides and $C_3$ to $C_6$ mono-olefins and mixtures thereof, and a hydrogen fluoride-containing alkylation catalyst comprising from about 40 to about 1 weight percent sodium polyacrylate and from about 60 to about 99 weight percent hydrogen fluoride, at a temperature from about −30° C. to about 100° C. and a pressure of from about 15 psia to about 315 psia for a contact time suitable to form a reaction mixture comprising a hydrocarbon phase, the hydrocarbon phase comprising an alkylate product, and a catalyst phase;

(B) separating the hydrocarbon phase and the catalyst phase; and (C) processing the hydrocarbon phase to recover the alkylate product.

14. An alkylation process comprising the steps of:

(A) contacting a feedstock, comprising at least one hydrocarbon selected from the group consisting of paraffinic hydrocarbon, isoparaffinic hydrocarbon, aromatic hydrocarbon, and mixtures thereof and at least one selected from the group consisting of $C_3$ to $C_5$ alkyl halides and $C_3$ to $C_6$ mono-olefins and mixtures thereof, and a hydrogen fluoride-containing alkylation catalyst comprising from about 50 to about 20 weight percent of an acid salt selected from the group consisting of ammonium trifluoroacetate, ammonium sulfate, ammonium methanesulfonate, and mixtures thereof and from about 50 to about 80 weight percent hydrogen fluoride, at a temperature from about −30° C. to about 100° C. and a pressure of from about 15 psia to about 315 psia for a contact time suitable to form a reaction mixture comprising a hydrocarbon phase, the hydrocarbon phase comprising an alkylate product, and a catalyst phase;

(B) separating the hydrocarbon phase and the catalyst phase; and (C) processing the hydrocarbon phase to recover the alkylate product.

15. The process of claim 14 wherein the acid salt is ammonium sulfate.

16. The process of claim 14 wherein the acid salt is ammonium methanesulfonate.

17. An alkylation process comprising the steps of:

(A) contacting a feedstock and a hydrogen fluoride-containing alkylation catalyst, the catalyst comprising an effective amount of sodium polyacrylate and a catalytic amount of hydrogen fluoride, under conditions suitable to form a reaction mixture comprising a hydrocarbon phase, the hydrocarbon phase comprising an alkylate product, and a catalyst phase:

(B) separating the hydrocarbon phase and the catalyst phase; and (C) processing the hydrocarbon phase to recover the alkylate product.

18. The process of claim 17 wherein the sodium polyacrylate is present in an amount of from about 40 to about 1 weight percent and the hydrogen fluoride is present in an amount of from about 60 to about 99 weight percent.

19. The process of claim 17 wherein the sodium polyacrylate is present in an amount of from about 30 to about 1 weight percent and the hydrogen fluoride is present in an amount of from about 70 to about 99 weight percent.

20. An alkylation process comprising the steps of:

(A) contacting a feedstock and a hydrogen fluoride-containing alkylation catalyst, the catalyst comprising an effective amount of ammonium trifluoroacetate and a catalytic amount of hydrogen fluoride, under conditions suitable to form a reaction mixture comprising a hydrocarbon phase, the hydrocarbon phase comprising an alkylate product, and a catalyst phase:

(B) separating the hydrocarbon phase and the catalyst phase; and (C) processing the hydrocarbon phase to recover the alkylate product.

21. An alkylation process comprising the steps of:

(A) contacting a feedstock, comprising at least one hydrocarbon selected from the group consisting of paraffinic hydrocarbon, isoparaffinic hydrocarbon, aromatic hydrocarbon, and mixtures thereof and at least one selected from the group consisting of $C_3$ to $C_5$ alkyl halides and $C_3$ to $C_6$ mono-olefins and mixtures thereof, and a hydrogen fluoride-containing alkylation catalyst comprising from about 50 to about 20 weight percent of ammonium trifluoroacetate and from about 50 to about 80 weight percent hydrogen fluoride, at a temperature from about −30° C. to about 100° C. and a pressure of from about 15 psia to about 315 psia for a contact time suitable to form a reaction mixture comprising a hydrocarbon phase, the hydrocarbon phase comprising an alkylate product, and a catalyst phase;

(B) separating the hydrocarbon phase and the catalyst phase; and (C) processing the hydrocarbon phase to recover the alkylate product.

* * * * *